United States Patent [19]

Miller et al.

[11] Patent Number: 4,483,446
[45] Date of Patent: Nov. 20, 1984

[54] SHELF FOR A STEAM ENVIRONMENT

[75] Inventors: William R. Miller, Erie, Pa.; Peter F. Staats, Brookfield, Wis.

[73] Assignee: American Sterilizer Company, Erie, Pa.

[21] Appl. No.: 439,860

[22] Filed: Nov. 8, 1982

[51] Int. Cl.³ .............................................. A47F 5/00
[52] U.S. Cl. ..................................... 211/153; 211/182
[58] Field of Search ................. 211/153, 182, 90, 134, 211/135

[56] References Cited

U.S. PATENT DOCUMENTS

| | | | |
|---|---|---|---|
| 600,879 | 3/1898 | Louden | 211/153 |
| 633,843 | 9/1899 | Hoyt | 211/153 |
| 676,381 | 6/1901 | Ball | 211/153 |
| 707,983 | 8/1902 | Taylor | 211/153 |
| 1,979,902 | 11/1934 | Potter et al. | 211/153 |
| 2,157,130 | 5/1939 | Hokanson | 211/153 |
| 2,428,718 | 10/1947 | Nauert | 211/153 |

FOREIGN PATENT DOCUMENTS 26378 of 1896 United Kingdom ................ 211/153

Primary Examiner—Ramon S. Britts
Assistant Examiner—Sarah A. Lechok
Attorney, Agent, or Firm—Robert D. Yeager; Andrew J. Cornelius; Christine R. Ethridge

[57] ABSTRACT

A shelf supports a load in such a steam environment as a steam sterilizer. The shelf includes at least one load supporting member which has a thermally efficient configuration. Accordingly, the shelf members may be tubular, may have channels with U-shaped cross sections, may be beams having an inverted T-shaped cross section or may be a tray having a plurality of U-shaped channels. Thus, the surfaces of each load supporting member are so adapted that formation of condensation on the surfaces is inhibited. In addition, the members are designed to retain at least a portion of the condensation formed on the surfaces of the members and direct to a desired location any condensation that cannot be held by the load supporting member.

2 Claims, 6 Drawing Figures

SHELF FOR A STEAM ENVIRONMENT

BACKGROUND OF THE INVENTION

1. Field of the Invention

The invention relates generally to a shelf for use in such a steam environment as a steam sterilizer and, more particularly, to a shelf for use in such a steam environment which is directed toward reducing the quantity of steam condensation that drips from the shelf.

2. Description of the Prior Art

Generally, a shelf used to support articles in such a steam environment as a steam sterilizer includes a plurality of solid rods or wires, usually made of metal, that are secured to apparatus for supporting the shelf within the steam environment.

One problem associated with the use of such a shelf is the condensation that forms on the shelf and drips onto the load supported by another shelf disposed below it. If, during a steam sterilization process, water drips onto such a load as a pack comprising articles to be sterilized that are wrapped in a permeable cloth, paper, or nonwoven material, the pack could absorb water. Such a load, commonly referred to as a "wet pack", is difficult to dry because it is not uniformly moist. If an incompletely dried sterile wet pack is removed from a sterile environment, the wet portion of the wrap might form a path along which bacteria could travel through the pack and contaminate the sterile articles. Thus, the sterilization cycle should include an extended drying period to dry any wet packs which may have been created during the cycle and ensure that the material inside the pack will remain sterile after the pack is removed from the sterilizer.

The problem identified above is caused by the relatively large quantity of condensation that forms on a shelf having solid metallic support rods or wires. The rods or wires must absorb a large amount of thermal energy from the surrounding steam before their temperature can rise to that of the environment. As thermal energy is transferred from the steam to the rods, some steam condenses and water forms on the rods. The greater the amount of energy required to raise the temperature of the rods to the temperature of the environment, the greater the amount of steam that must condense to supply the energy, and the greater the amount of water that is formed.

Accordingly, there is a need for a shelf for use in a steam environment that will inhibit the formation of condensation on the load supporting members of the shelf and that will prevent any condensation that does form on the members from dripping onto loads supported by other shelves.

SUMMARY OF THE INVENTION

The present invention provides a shelf for supporting a load in such a steam environment as a steam sterilizer. The shelf includes at least one load supporting member, each load supporting member having a thermally efficient configuration. The phrase "thermally efficient configuration" is used in the present application to refer to a configuration for a load supporting member that is structurally efficient, that is, the member has a thermal capacitance lower than that of a solid rod having a circular cross section and a strength equal to that of the rod. Therefore, the mass of the shelf and the amount of heat the shelf absorbs from the steam are less than those of a shelf constructed with the solid rods, and less condensation forms on the load supporting members than would form on the rods.

The members are configured to retain at least a portion of any condensation formed on a surface of each load supporting member and to direct away from the load any condensation that cannot be retained by the load supporting member.

In one embodiment, the load supporting member is an elongated, hollow rod coated on at least a portion of its outer surface with a material having heat insulating properties that will inhibit the formation of condensation on the outer surface of the load supporting member.

In another embodiment, the load supporting member has a surface facing upwardly and a surface facing downwardly during normal use of the shelf. The upwardly facing surface has a liquid retaining portion for retaining at least a portion of the condensation formed on the upwardly facing surface. Preferably, the member is elongated and has a U-shaped cross section, a beam with an inverted T-shaped cross section, or a tray having a plurality of parallel U-shaped channels extending along the tray and defining slits disposed parallel to and between the channels.

DETAILED DESCRIPTION OF THE PREFERRED EMBODIMENT

Figure 1:
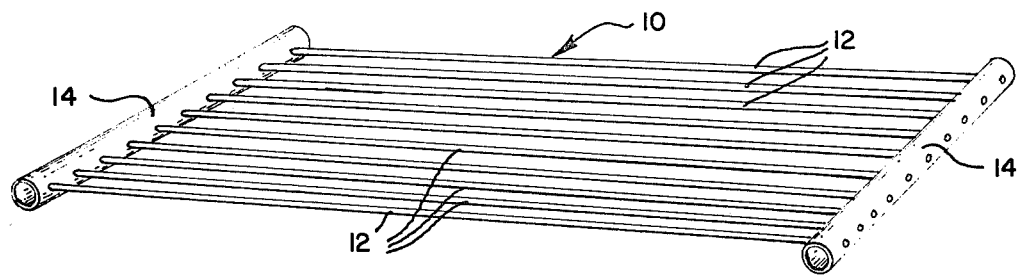
FIG. 1 is an isometric view of a sterilizer shelf constructed in accordance with the teachings of the present invention.

With reference to the drawings, the preferred shelf of the present invention, generally indicated by the reference numeral 10, is suitable for use in a steam sterilizer and includes load supporting members 12 and side supports 14, all formed from a suitable metal.

Figure 6:
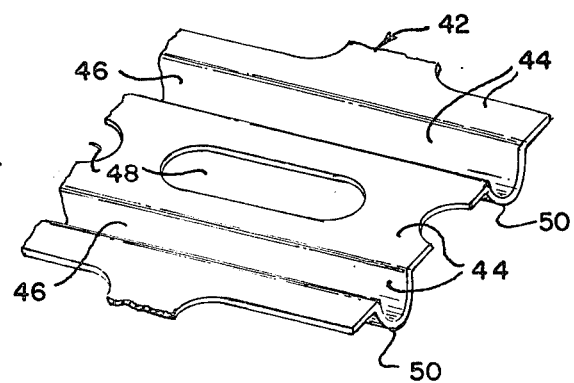
FIG. 6 is an isometric view of a portion of a load supporting member of another embodiment of the present invention.

Load supporting members 12 are formed in a thermally efficient configuration. Preferably, load supporting members 12 are tubular in shape as shown in FIG. 2, or channels as shown in FIG. 4, beams as shown in FIG. 5, or tray sections as shown in FIG. 6.

Figure 2:
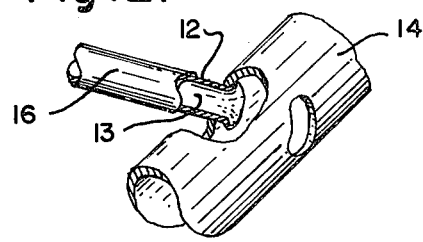
FIG. 2 is a cutaway view of a portion of the shelf shown in FIG. 1 showing a load supporting member of the shelf.
Figure 3:
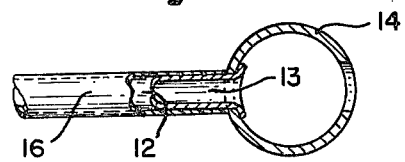
FIG. 3 is a partial sectional view of the sterilizer shelf shown in FIG. 1 taken along the line III—III.

With reference to FIG. 2, load supporting member 12 has a tubular cross section. The outer surface of member 12 is covered with a coating 16 of such material having heat insulating properties as aluminum impregnated with a fluorine-containing resin of the type sold under the trademark TEFLON. Coating 16 does not absorb heat as readily as the material used to form member 12. As the temperature of member 12 increases due to the presence of the steam within the sterilizer, coating 16 will absorb less thermal energy from the steam than will be absorbed by member 12. Thus, most of the condensation that forms on member 12 will form on the exposed inner surface 13 of member 12 and will be retained within member 12. Condensation in excess of the amount which can be retained within member 12 is directed to hollow side supports 14 which in turn direct the excess condensation to the corners of the sterilizer chamber. Shelf 10 is particularly useful in vacuum steam sterilizers because of the absence within the sterilizer of any air that could enter the interior of member 12 and block fluid flow therethrough.

Figure 4:
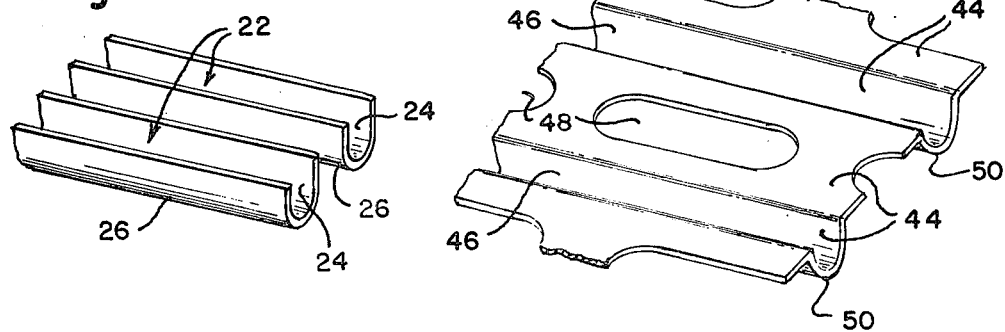
FIG. 4 is an isometric view of a portion of a load supporting member of another embodiment of the present invention.

In a second embodiment, shown in FIG. 4, each load supporting member 12 is a channel 22 having a U-shaped cross section that includes a concave upwardly facing surface 24. Any condensation that forms on upwardly facing surface 24 will be retained within channel 22. Downwardly facing surface 26 may be coated with the heat insulating material described above to ensure that most of the condensation formed on member 22 will be formed on upwardly facing surface 24.

Figure 5:
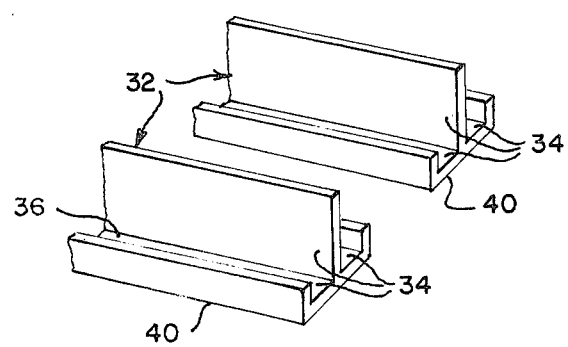
FIG. 5 is an isometric view of a portion of a load supporting member of another embodiment of the present invention.

In another embodiment, shown in FIG. 5, each load supporting member 12 is a beam 32 having an inverted T-shaped cross section that includes upwardly facing surfaces 34 that define liquid retaining portions 36. Any condensation that forms on upwardly facing surfaces 34 will be retained within liquid retaining portions 36 of beam 32. Downwardly facing surfaces 40 may be coated with the heat insulating material described above to ensure that most of the condensation formed on member 32 will be formed on upwardly facing surfaces 34.

In another embodiment, shown in FIG. 6, load supporting member 12 is a tray section 42 having upwardly facing surfaces 44 defining a plurality of parallel U-shaped channels 46 extending along tray section 42 and a plurality of slits 48 disposed parallel to and between channels 46. Channels 46 retain condensation formed on upper surfaces 44 of tray section 42. Slits 48 permit circulation of the steam within the sterilizer chamber. Downwardly facing surfaces 50 may be coated with the heat insulating material described above to ensure that most of the condensation formed on tray section 42 will be formed on upwardly facing surfaces 44.

What is claimed is:

1. A shelf for supporting a load in a steam environment comprising:
    at least one load supporting member, each said load supporting member having an upwardly facing surface and a downwardly facing surface during normal use of said shelf, said upwardly and downwardly facing surfaces being configured for such thermal efficiency that the formation of condensation is inhibited on at least one of said surfaces of each said load supporting member, said upwardly facing surface having a U-shaped cross section for retaining at least a portion of the condensation formed on said upwardly facing surface, and said downwardly facing surface being coated with a material that impedes heat flow; and
    means for fixing the location of each said load supporting member within the steam environment.

2. The shelf recited in claim 1 further comprising means for directing to a desired location any condensation that cannot be retained by a said load supporting member.

* * * * *